United States Patent [19]

Kaasenbrood

[11] Patent Number: 4,486,270
[45] Date of Patent: Dec. 4, 1984

[54] APPARATUS FOR THE REMOVAL OF AMMONIUM CARBAMATE FROM A UREA-SYNTHESIS SOLUTION

[75] Inventor: Petrus J. C. Kaasenbrood, Sittard, Netherlands

[73] Assignee: Unie Van Kunstmestfabrieken B.V., Utrecht, Netherlands

[21] Appl. No.: 312,662

[22] Filed: Oct. 19, 1981

Related U.S. Application Data

[62] Division of Ser. No. 223,210, Jan. 7, 1981, abandoned.

[30] Foreign Application Priority Data

Nov. 30, 1977 [NL] Netherlands .......................... 7713190

[51] Int. Cl.³ ............................................... B01D 3/34
[52] U.S. Cl. ...................................... 202/201; 165/96; 165/111; 165/139; 202/203

[58] Field of Search ..................... 260/555 B; 202/201, 202/203; 562/555; 165/110, 111, 139, 96

[56] References Cited

FOREIGN PATENT DOCUMENTS 212014 5/1908 Fed. Rep. of Germany .

Primary Examiner—Frank Sever

[57] ABSTRACT

An improved process and apparatus for the removal of ammonium carbamate from an aqueous urea solution wherein the aqueous urea solution is introduced into a stripping zone and caused to flow down a heat exchange wall as a thin film while being heated and contacted in counter-current relation with a gaseous stripping agent. The aqueous urea solution, while being stripped, is heated for at most 5 seconds at a temperature in the range of from 180°–195° C. and thereafter cooled to a temperature of from 155°–170° C.

2 Claims, 1 Drawing Figure

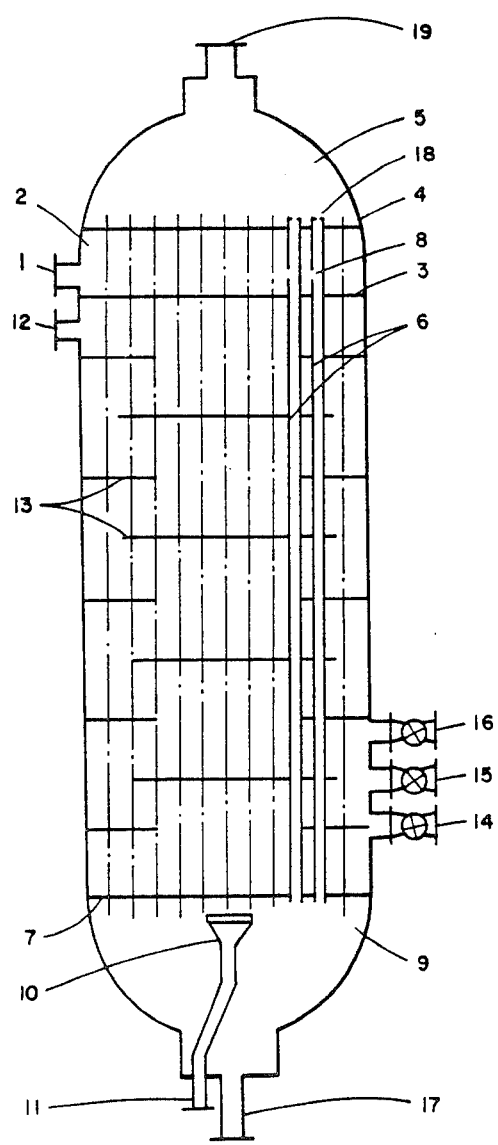

APPARATUS FOR THE REMOVAL OF AMMONIUM CARBAMATE FROM A UREA-SYNTHESIS SOLUTION

This is a division of application Ser. No. 223,210 filed Jan. 7, 1981, now abandoned.

BACKGROUND OF THE INVENTION

The invention relates to a process for the removal of ammonium carbamate from an aqueous urea solution containing ammonium carbamate such as the urea-synthesis solution resulting from the synthesis of urea from ammonia and carbon dioxide at elevated temperature and pressure. The aqueous urea solution is made to flow down a wall as thin film at a pressure of 120–180 atmospheres at a temperature of 170°–200° C. in counter-current relation to a gaseous stripping agent, while heat is applied, and the stripped aqueous urea solution and the resulting gaseous mixture formed in stripping are discharged by way of a liquid collecting chamber and a gas collecting chamber, respectively.

A stripping process of this type is described in U.S. Pat. No. 3,356,723 wherein a urea-synthesis solution is contacted with gaseous carbon dioxide in counter-current flow with heating, preferably at the urea-synthesis pressure. It is also stated that such a stripping process can be carried out by means of a gaseous ammonia stripping agent, although not as advantageously.

By adding gaseous carbon dioxide to the gas phase at equilibrium with the solution being stripped, the composition of the gas phase is changed so that it is no longer in equilibrium with the solution. As a result, part of the ammonium carbamate contained in the liquid phase decomposes and the ammonia and carbon dioxide thus formed pass into the gas phase in order to restore the heterogeneous equilibrium. This desorption results in the equilibrium between ammonium carbamate, urea and water in the liquid phase being disturbed, which in turn causes part of the urea that has already formed to hydrolyze back into the starting products ammonia and carbon dioxide.

The rate of such hydrolysis of urea increases with temperature. For this reason the temperature at which the stripping treatment is effected in the known process is kept comparatively low, and the retention time of the urea-synthesis solution in the stripping zone is kept relatively short by use of a wetted wall heat exchanger. Nevertheless, hydrolysis of urea does occur and this has an unfavorable influence on the conversion to urea, and consequently on the efficiency of the overall process for preparing urea in which the stripping treatment is used.

Another secondary reaction that takes place during and as a consequence of the stripping treatment is the formation of biuret, a compound that will cause damage to plants when contained in urea fertilizer in too high a concentration. For this reason, the biuret content of solid urea used for fertilizer purposes must not exceed 2.5% by weight, and should be no higher than 0.3% by weight in fertilizer solutions that are to be applied to the leaves. The biuret content of the final product is also a function of both time and temperature, increasing with increases in temperature and the time during which a urea-synthesis solution is treated to decompose unconverted ammonium carbamate and desorb the resulting ammonia and carbon dioxide.

Thus, in order to reduce both the hydrolysis of urea and the conversion of urea into biuret, it is desirable to minimize the time at which the urea-synthesis solution is exposed to high temperatures. On the other hand, it is necessary to maintain the urea-synthesis solution at an elevated temperature for some period of time in order to effectively decompose the ammonium carbamate and desorb the resulting ammonia and carbon dioxide.

It is therefore an object of the present invention to provide a process and apparatus whereby it is possible to minimize the undesirable hydrolysis of urea and formation of biuret while at the same time sufficiently decomposing the ammonium carbamate and removing it from the aqueous urea solution.

BRIEF DESCRIPTION OF THE INVENTION

In a stripping treatment such as described above, the temperature of the urea-synthesis solution is raised due to the application of heat, with the result that the equilibrium of ammonium carbamate with urea and water, represented by

$$NH_2COONH_4 \rightleftharpoons NH_2CONH_2 + H_2O,$$

is shifted toward the right, that is, favoring the formation of urea. Under the same conditions, the ammonium carbamate is decomposed into ammonia and carbon dioxide with the result that the equilibrium is shifted toward the left favoring the undesirable hydrolysis of urea. It has now been found, however, that under such conditions the amount of urea formed is approximately equal to the amount of urea that hydrolyzes, but only during the initial period of heating up to at most 5 seconds. Further heating at relatively high temperatures for longer times result in more rapid urea hydrolysis than urea formation, leading to a net reduction in the amount of urea in the aqueous urea solution. It has been found, however, that if the stripping treatment is continued after the initial period of heating, but with the removal of heat, the decomposition and desorption of ammonium carbamate will continue, but the rate of hydrolysis of urea is reduced to an acceptable level.

These findings are carried into practice, according to the process of the present invention, by introducing the aqueous urea solution into the stripping zone as a thin film flowing down a heat exchange wall, and heating and maintaining this aqueous urea solution at a temperature in the range of from 180°–195° C. for at most 5 seconds, while stripping with a counter-current flow of a gaseous stripping agent. The resulting heated aqueous urea solution is thereupon cooled down to a temperature in the range of between 155° C.–170° C., while still being contacted with the gaseous stripping agent, before falling into the liquid collecting chamber at the bottom of the stripping zone. Preferably, this cooling with simultaneous stripping should continue for about 1 to 2 seconds.

The heating and subsequent cooling of the aqueous urea solution film in the stripping zone may be accomplished by heating the upper portion of the heat exchange wall with a first liquid or gas, and cooling the lower portion of the heat exchange wall by means of a second liquid or gas. Preferably, however, a condensable gas such as steam is used as the heating agent to heat the wall, and thus the film of aqueous urea solution flowing down the other side of the wall. The subsequent cooling can be effected by permitting the condensate formed to build up to a controlled level at the bottom portion of the heat exchange wall thus retarding the heat exchange to the aqueous urea solution. Here the cooling of the aqueous urea solution is primarily due to the substantially continued endothermic decomposition of ammonium carbamate resulting from the continued contact of the cooling urea-synthesis solution with the stripping agent. However, direct cooling may be applied as well by means of the stripping agent, which usually has a considerably lower temperature than the heated urea-synthesis solution. Best results are obtained when the temperature of the stripping agent is in the range of between about 80° and 125° C.

A further reduction in the hydrolysis of urea and formation of biuret can be achieved by minimizing the time between the moment at which the stripped urea-synthesis solution flows into the collecting chamber and the moment at which the pressure on the solution is reduced after leaving the collecting chamber, thus resulting in a further temperature drop. This can be achieved by keeping the retention time of the stripped urea-synthesis solution in the liquid collecting chamber shorter than 25 seconds. However, there must be some retention time in this liquid collecting chamber in order to provide sufficient liquid level for adequate level control within the collecting chamber, thus preventing the escape of gas through the subsequent expansion valve in the liquid outflow line.

The invention also relates to apparatus specifically devised and adapted for carrying out the above process. This apparatus consists of a tubular heat exchanger vertically disposed within the interior of a shell or jacket. This apparatus is provided with means for introducing the aqueous urea solution to be stripped into the upper end of the tubes, and means for distributing such solution so that it flows down as a film along the inner wall surface of such tubes. The stripped aqueous urea solution is collected at the bottom of the tubes and discharged from the apparatus. Means are also provided for introducing the gaseous stripping agent into the lower portion of the heat exchange tubes and causing it to flow in an upward direction through the tubes. The stripping gas, together with the gases stripped out of the solution, are collected at the top of the tubes and discharged from the apparatus. Means for heating the tubes are also provided, comprising a heating chamber or jacket space defined by an upper and lower tube sheet or partition through which the tubes extend, the outer wall surface of the tubes and the jacket itself, and such chamber is provided with inlet means for the gaseous heating agent, and outlet means for the condensate. In accordance with the improvement of the invention the outlet means for discharging the condensate is comprised of a plurality of condensate outlet openings through the jacket at varying heights above the lower tube sheet. These outlet openings are adapted so as to permit the accumulation of condensate in the bottom of the chamber above the tube sheet, and control of the level of this condensate by, for example, providing the condensate openings with independently closable valves.

DETAILED DESCRIPTION OF THE INVENTION

The invention will be further illustrated with reference to the drawing, which diagrammatically shows a longitudinal section through a stripping apparatus that is suitable for carrying out a preferred variant of the process according to the present invention. In this apparatus, the urea-synthesis solution to be treated, having a temperature of between about, for example, 180° and 185° C., is fed to the stripping apparatus through inlet 1 leading into liquid-distributing space 2 between the upper tube sheet or plate 3 and wall 4. Wall 4 separates this liquid distributing space 2 from gas collecting chamber 5. The pressure at which the solution is treated may be at the urea-synthesis pressure, for example, 140 atmospheres absolute. If higher synthesis pressures are used, the urea-synthesis solution may first be expanded if desired before being fed to the stripping apparatus. From the liquid distributing space 2, the solution is uniformly distributed over the tubes 6 that are fitted in the upper tube sheet 3 and the lower tube sheet 7. Only two such tubes are diagrammatically shown on the drawing, but it should be understood that there may be many hundreds of such tubes. The head of each tube is equipped with a liquid distributor which so distributes the urea-synthesis solution over the inner wall surface of the tube that it flows down as a thin film. For the sake of simplicity, the liquid distributors are indicated by openings 8.

A preferred tube length is between about 6 and 8 meters, and the internal diameter is preferably 20 to 30 mm. In such case, the liquid load per tube should be maintained at approximately 80 to 90 kg/hour to avoid flooding. The solution flows down the inner wall surface of the tube 6 with a speed of about 1 meter per second.

The urea-synthesis solution flowing down the tubes is in counter-current relation to a stripping gas, which may be carbon dioxide, ammonia, an inert gas or a mixture of these gases. This stripping gas having a temperature of, for instance, 120° C., is introduced into the apparatus from distributor 10 on feed pipe 11 through the liquid collecting chamber 9 and into the bottom portion of the tubes.

The heat required for the decomposition of the ammonium carbamate in the urea-synthesis solution is obtained by heating the tubes 6 by means of a gaseous or liquid heating agent that is fed through inlet 12 into the upper portion of the shell or jacket side of the stripping apparatus, outside of the tubes, which will be referred to herein as the jacket space. To effect proper heat transfer, partitions or baffles 13 have been mounted in the jacket space. The stripping apparatus here shown is equipped for the use of saturated steam as the heating agent, having a temperature of, for example, 210° to 220° C. The steam condenses in the jacket space of the stripping apparatus, and the resulting condensate is discharged through one of the outlets 14, 15 or 16 which are fitted through the shell at various heights above the lower tube sheet. These condensate outlets may be independently closable so as to permit control of the depth of condensate accumulating over the lower tube sheet. The urea-synthesis solution flowing down the inner wall surface of tubes 6 is thus heated from the point where such tubes pass through upper tube sheet 3 down to the level of condensate surrounding such tubes, permitting the temperature of the urea-synthesis solution to rise to about 195° C. When this solution reaches the portion of tubes surrounded by condensate, no further heat is applied, and due to contact with the comparatively cold stripping gas and the endothermic effect of the continuing stripping action, heat is given off or consumed by the decomposition of ammonium carbamate and evaporation of the ammonia and carbon dioxide thus released. The heated urea synthesis solution is thus cooled as it flows down through the portion of tube 6 surrounded by condensate. If desired, the cooling effect may be increased by lowering the temperature of the condensate by the addition of colder water. The level at which the condensate is drained from the jacket space, and thus the level of condensate within the jacket space, is so chosen that the urea-synthesis solution flowing down the inner wall surface of tubes 6 will reach the condensate level in at most 5 seconds.

In principle it is also possible to heat and subsequently cool the urea-synthesis solution flowing down the inner wall surface of tubes 6 by separate gases or liquids. In such event, the jacket space of the stripping apparatus may be fitted with a horizontal partition that fully separates the heating zone from the cooling zone. A hot gas, such as saturated steam, may be used as the heating agent, while the cooling agent may be, for example, process condensate or boiler feed water that have to be heated, thereby directly utilizing the discharged heat. This embodiment, however, has the disadvantage that it is more difficult to change the time period of heating of the urea-synthesis solution by variation of the height of the heating zone as compared to the embodiment illustrated in the FIGURE.

The stripped urea-synthesis solution flowing from tube 6 and having a temperature of, for example, 160° C. is collected in liquid collecting chamber 9, from which it is discharged as quickly as possible, preferably within 20 to 25 seconds, through outlet 17. However, a minimum liquid level must be maintained in liquid collecting chamber 9 in order to prevent stripping gas from being discharged through outlet 17 together with the stripped urea-synthesis solution. A very low and still effective liquid level can be obtained by fitting a vortex breaker over outlet 17, thus permitting a very short retention time of the liquid in collecting chamber 9. To further reduce the harmful effect of retaining stripped urea-synthesis solution in liquid collecting chamber 9, one or more heat exchange members may be fitted in this chamber to cool the stripped urea-synthesis solution.

The ammonia and carbon dioxide stripped from the urea-synthesis solution by the stripping treatment, and a relatively small equilibrium amount of water vapor, are passed together with the stripping agent from the top of tubes 6 through opening 18 into gas collecting chamber 5, from which they are passed through outlet 19 to, for example, a condenser or back to the urea reactor.

What is claimed is:

1. In an apparatus for the counter-current stripping of ammonium carbamate from an aqueous urea solution by means of a gaseous stripping agent, said apparatus comprising a tubular heat exchanger having a plurality of tubes with inner and outer wall surfaces vertically disposed within the interior of a jacket and extending between and through an upper and a lower tube sheet, a gas collecting chamber in fluid communication with the upper portion of said tubes, and a liquid collecting chamber in fluid communication with the lower portion of said tubes, said apparatus being further provided with:

means for introducing said aqueous urea solution into the upper portion of said tubes and causing it to flow down said inner wall surface as a film;
   means for introducing said gaseous stripping agent into the lower portion of said tubes and causing it to flow upward through said tubes; and
   means for heating said tubes comprising a jacket space defined by said upper and lower tube sheets, the outer wall surface of said tubes and said jacket, and inlet means for introducing a gaseous condensable heating agent into said jacket space, and outlet means for discharging of condensate from said jacket space;

the improvement comprising, elements designed, dimensioned and arranged for the counter-current stripping of ammonium carbamate from an aqueous urea solution by means of a gaseous stripping agent, including, said jacket space outlet means is adapted to permit control of the condensate level within said jacket space at varying heights above said lower tube sheet;
   said liquid collecting chamber is provided with means for maintaining a predetermined minimum liquid level therein; and
   said liquid collecting chamber is further provided with at least one heat exchange member adapted to cool the liquid collected in said liquid collecting chamber.

2. In an apparatus for the counter-current stripping of ammonium carbamate from an aqueous urea solution by means of a gaseous stripping agent, said apparatus comprising a tubular heat exchanger having a plurality of tubes with inner and outer wall surfaces vertically disposed within the interior of a jacket and extending between and through an upper and lower tube sheet, a gas collecting chamber in fluid communication with the upper portion of said tubes, and a liquid collecting chamber in fluid communication with the lower portion of said tubes, said apparatus being further provided with:

means for introducing said aqueous urea solution into the upper portion of said tubes and causing it to flow down said inner wall surface as a film;
   means for introducing said gaseous stripping agent into the lower portion of said tubes and causing it to flow upward through said tubes; and
   means for heating said tubes comprising a jacket space defined by said upper and lower tube sheets, the outer wall surface of said tubes and said jacket, and inlet means for introducing a gaseous condensable heating agent into said jacket space, and outlet means for discharge of condensate from said jacket space;

the improvement comprising, elements designed, dimensioned and arranged for the counter-current stripping of ammonium carbamate from an aqueous urea solution by means of a gaseous stripping agent, including, said jacket space outlet means comprised of a plurality of condensate outlet openings through said jacket at varying heights above said lower tube sheet, which are adapted to be independently closable;
   said liquid collecting chamber is provided with means for maintaining a predetermined minimum liquid level therein; and
   said liquid collecting chamber is further provided with at least one heat exchange member adapted to cool the liquid collected in said liquid collecting chamber.

* * * * *